US012446952B2

(12) United States Patent
Bromley

(10) Patent No.: US 12,446,952 B2
(45) Date of Patent: Oct. 21, 2025

(54) SMOKE EVACUATION PENCIL

(71) Applicant: Robert Lee Bromley, El Paso, TX (US)

(72) Inventor: Robert Lee Bromley, El Paso, TX (US)

(*) Notice: Subject to any disclaimer, the term of this patent is extended or adjusted under 35 U.S.C. 154(b) by 599 days.

(21) Appl. No.: 17/809,559

(22) Filed: Jun. 29, 2022

(65) Prior Publication Data

US 2024/0000502 A1 Jan. 4, 2024

(51) Int. Cl.
*A61B 18/14* (2006.01)
*A61B 18/00* (2006.01)

(52) U.S. Cl.
CPC .. *A61B 18/148* (2013.01); *A61B 2018/00202* (2013.01); *A61B 2018/00589* (2013.01); *A61B 2018/00601* (2013.01); *A61B 2018/00607* (2013.01); *A61B 2018/0091* (2013.01); *A61B 2018/1475* (2013.01); *A61B 2218/008* (2013.01)

(58) Field of Classification Search
CPC ........... A61B 2018/00196; A61B 2018/00589; A61B 2018/00601; A61B 2018/00607; A61B 2018/0091; A61B 2018/1475; A61B 18/148; A61B 2218/008
See application file for complete search history.

(56) References Cited

U.S. PATENT DOCUMENTS

| | | | | |
|---|---|---|---|---|
| 2009/0018539 A1* | 1/2009 | Cosmescu | A61M 39/1055 606/41 |
| 2016/0346032 A1* | 12/2016 | Cosmescu | A61B 18/1402 |
| 2018/0333194 A1* | 11/2018 | Greep | A61B 18/1402 |
| 2018/0333195 A1* | 11/2018 | Greep | A61B 18/148 |
| 2022/0117646 A1* | 4/2022 | Kleyman | A61M 1/76 |

* cited by examiner

*Primary Examiner* — Linda C Dvorak
*Assistant Examiner* — Bradford C. Blaise

(57) ABSTRACT

A smoke evacuation pencil having an internal rotatable smoke evacuation channel with the distal end opening directly connected to the proximal end smoke hose fitting without a proximal seal and the distal end opening located at or near the distal nose of the surgical pencil overlapping an active electrode forming a one-piece channel. The internal smoke evacuation channel having a sufficient length to diameter ratio creating a near friction free rotation of the internal smoke evacuation channel. The seamless internal channel from proximal end to distal end eliminates the need for seals or friction fits commonly found on prior art smoke evacuation pencils having multi-part smoke evacuation swivel components.

5 Claims, 3 Drawing Sheets

SMOKE EVACUATION PENCIL

BACKGROUND OF INVENTION

Prior art surgical pencils use energy during surgical procedures having two modalities: one for cutting and one for coagulation. The energy used by surgical pencils comes from an electrosurgical generator creating high frequency physiological tissue effects resulting in smoke plumes. Two main types of energy based surgical pencils fall into the category of electrosurgical pencils. One type is a foot activated pencil which does not have hand control buttons on the pencil body. Another type is a hand control button pencil. For all electrosurgical pencils an active electrode is attached to the distal end of the surgical pencil as the conductor directing the high frequency energy to the patient site. Concerns by operating room personnel are present as inhaled smoke plumes can have potentially harmful long term health effects. These concerns raise awareness in the use a smoke evacuation means either being attached to or integrated in an electrosurgical pencil to evacuate smoke plumes. Prior art smoke evacuation pencils have incorporated distal end openings and cooperative smoke channels, that are generally hollow for smoke flow; thereby, making the surgical pencil larger compared to a non-smoke evacuating surgical pencil and results in many complaints by surgeons regarding the larger size obstructing the surgeons view of a surgical site. Smoke evacuating pencils also have additional weight at the proximal end which incorporates an electrical wire routed through a flexible smoke evacuation hose attached to the proximal end swivel of a surgical pencil causing discomfort in the retention and manipulation of the surgical pencil. Prior art surgical pencils were typically constructed with multiple components affecting the functional concern of suction loss due to seam leakage within the suction flow channel.

Assembly methods have variations; one is a hollow body smoke channel with a swiveling proximal smoke hose fitting with a seal typically an O ring, which creates friction when swiveling and minimizes suction loss, a two part body housing to seat the O ring seal, an inner hollow channel formed by the two part body that does not rotate which may or may not integrate electrical contact to the active electrode, and a distal nose that may or may not include an extendable telescopic section commonly understood by those skilled in the art where a extendable telescopic section has linear stops to limit the extended length. An extendable telescopic section reciprocates between two positions, retracted and extended having a cooperative smoke evacuation channel. The outer body is usually constructed in two halves and must be sealed together to prevent suction loss. A hand controlled surgical pencil must also include a sealing means around the two hand control buttons.

Another prior art method of assembly is the use of an internal channel that mounts the active electrode socket at the distal end. The socket is electrically connected by a wire to the electrosurgical generator. Since the internal channel has a socket for the active electrode it cannot rotate in conjunction with the proximal end swivel fitting. The seam between the internal channel and the proximal end swivel fitting must have a seal or a tight tolerance fit to prevent suction leakage. Also, the proximal end swivel fitting must have a seal to the main body of the smoke evacuating pencil causing friction. The body of the smoke evacuating pencil is normally firmly held by the surgeon's hand. The active electrode may independently rotate within the active electrode socket and once set by the surgeon it will not rotate until the desired tissue effect is obtained.

The pencil position in the surgeons hand is held in place by the index finger and opposing thumb with the main pencil body resting on the crook of the hand.

Two major complaints about smoke evacuation pencils are: the proximal end swivel fitting has resistance to pencil rotation about the longitudinal axis of the pencil, and the included weight of a 2 meter long suction hose imposing a force downward, due to gravity, at the proximal end of the surgical pencil causing the distal end to rise out of the surgeon's hand pivoting about the crook of the hand acting as a pivot similar to a seesaw. The surgeon must grasp the pencil distally with increasing force to retain the pencil in the surgeon's hand. Fatigue in the surgeon's grip between the index finger and thumb is a primary cause of hand cramps compared to the less fatiguing non-smoke evacuating pencils which do not have a smoke evacuation hose.

Once the surgical pencil is placed in the hand various anatomical targets of and within a patient's body may cause the surgeon's forearm position and wrist rotation to create acute and obtuse angles to the surgeon's line of sight. In this embodiment the tedious angle changes of the surgical pencil primarily in rotation along the longitudinal axis eventually causes fatigue in the wrist due to the added weight and resistance of a smoke evacuation hose attached to a tight tolerance fit proximal end swivel of the surgical pencil. The drape of the suction hose creates disadvantageous leverage at various angles to the longitudinal axis increasing torque against the surgeon's grip.

CONCLUSION

In this novel invention, the disclosed internal seamless rotatable smoke flow channel from the distal end to the proximal end opening is freely rotatable inside a smoke evacuation pencil to allow optimized inline smoke evacuation without friction fits or seals to minimize the torque friction and fatigue commonly found on prior art multi-part internal swivels of smoke evacuation pencils.

SUMMARY OF THE INVENTION

A novel invention primarily concerned with smoke evacuation surgical pencils having an internal seamless rotatable smoke flow channel from the proximal end to the distal inlet for a continuous suction pathway thereby eliminating the required seals to prevent suction loss as compared to leakage encountered in multi-part smoke flow swivels. The proximal end swivel is press fit directly to an elastomeric smoke evacuation hose that is press fit connected to a suction source and the distal inlet of the internal smoke channel overlaps the active electrode of the surgical pencil for smoke intake. The diameter to distance ratio and elimination of friction fits or O ring seals allows a near frictionless (slip fit) swivel of the internal seamless channel. The frictionless rotation helps reduce the longitudinal axis torque encountered by the hanging smoke evacuation hose. The rotatable seamless internal smoke channel may or may not be connected to electrical connections and is rotatable which may or may not include a telescopic section within the internal seamless rotatable smoke flow channel. All of the components of this new and novel invention is manufactured using common thermoplastic molding techniques familiar to those skilled in the art of manufacturing smoke evacuation pencils. This embodiment does not include the descriptions of the electrical wiring of the smoke evacuation pencil with hand control buttons or foot control means as the circuit connections is typical and readily understood by those skilled in the art.

DETAILED DESCRIPTION OF DRAWINGS

Figure 1:
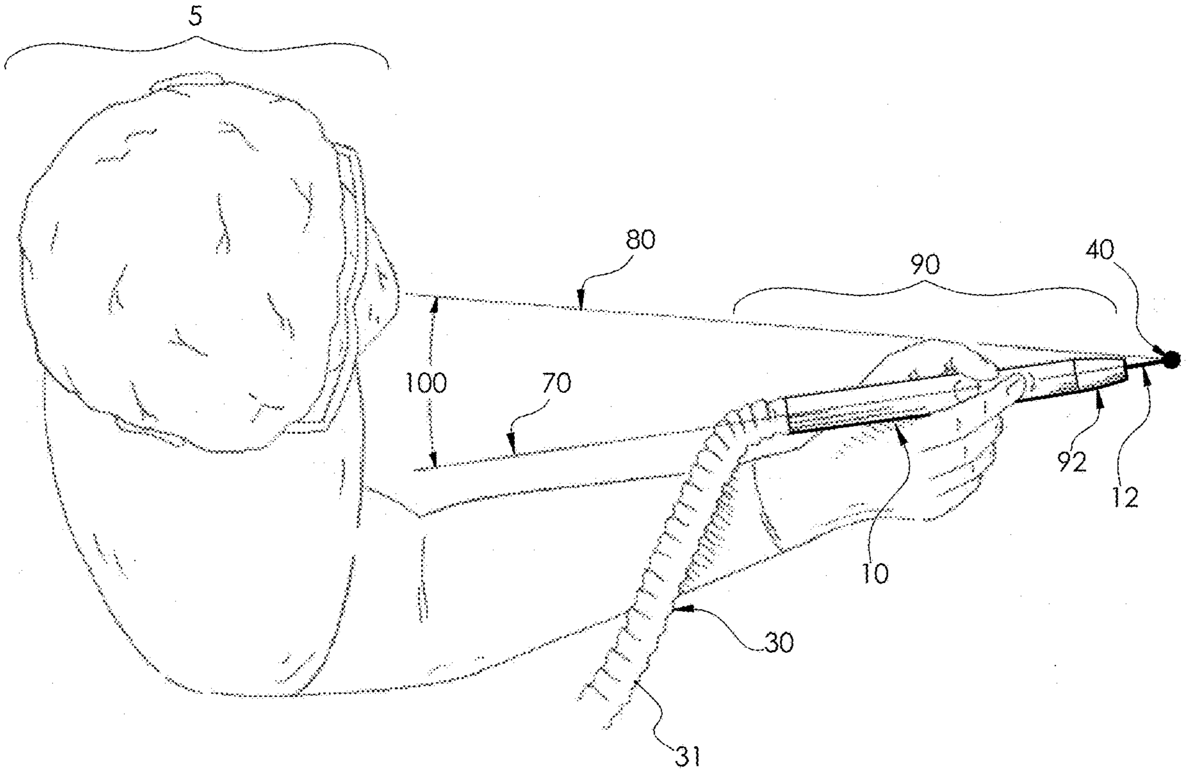
FIG. 1 is a top view of a surgeon holding a smoke evacuating surgical pencil with a smoke evacuation hose.

FIG. 1 is a plan view of a surgeon 5, holding a hand control smoke evacuating surgical pencil 90, having a proximal end smoke evacuating hose 30, depicting an acute angle 100 between the surgeon line of sight 80 and the longitudinal axis 70 of the smoke evacuating surgical pencil 90, as positioned so that the main body of the smoke evacuating surgical pencil 90 is resting on the crook of the hand 10, and depicting the drape of the smoke evacuation hose away from the proximal end of the smoke evacuating surgical pencil 90.

The hand control buttons are operated by the surgeon's index finger and require sealing to prevent suction loss around the two buttons under the index finger. When hand control buttons are operated a smoke plume originates from the patient site 40 as it is energized through conduction of the active electrode 12 projecting from the distal nose 92 of the pencil body 90.

Figure 2:
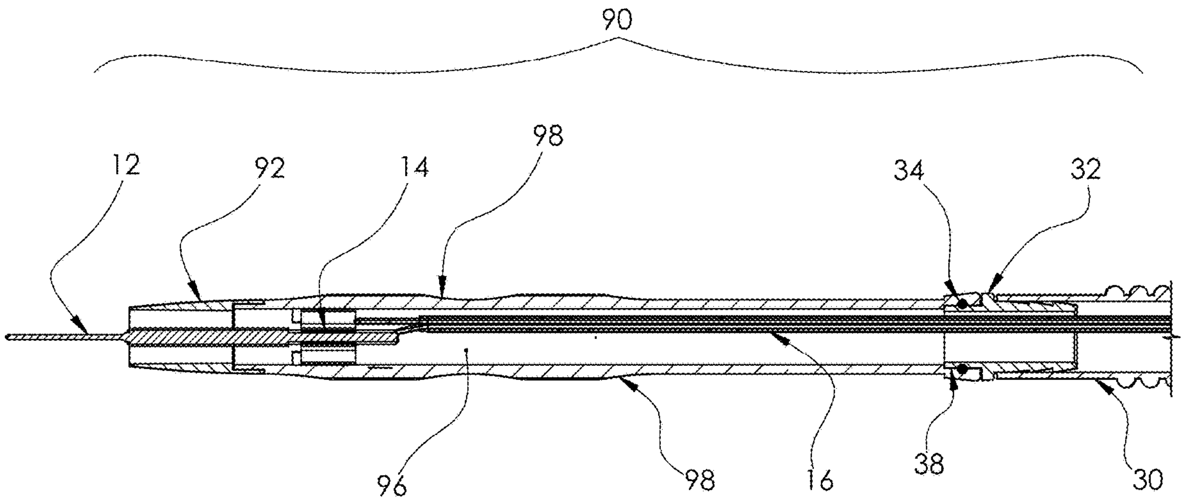
FIG 2 PRIOR ART
FIG. 2 is a top view cross section of a prior art smoke evacuation hollow pencil body with seals.

FIG. 2 is a top view cross section of prior art smoke evacuation pencils showing a typical construction means.

The construction as described from distal to proximal end comprising; a metallic conductor called an active electrode 12, an active electrode socket 14 connected to a wire 16, a distal end nose 92 typically made of clear material attached to a hollow pencil body 98 of the smoke evacuating pencil 90, a non-rotating hollow smoke channel 96 formed by the hollow pencil body 98, a proximal end swivel fitting 32 and swivel seal 34 trapped within a groove found on the proximal end swivel fitting 32 outside diameter seal 38 having a tight tolerance fit at the distal end of swivel fritting 32, and an inside diameter groove in the hollow pencil body 98, and attached to the proximal end swivel fitting 32 is the smoke evacuating hose 30. Suction flows from the distal end 92 passed the active electrode 12, and socket 14, into a non-rotating hollow smoke channel 96 of surgical pencil body 98 through the proximal end swivel fitting 32 and into the smoke evacuating hose 30. The hollow pencil body 98 is usually made of two halves and requires the two halves to be sealed usually by ultrasonic welding to prevent leakage. The proximal swivel end fitting 32 rotates in respect to the smoke evacuating pencil 90 and has an O ring 34 and seal 38 to minimize suction loss but increases swivel friction.

Figure 3:
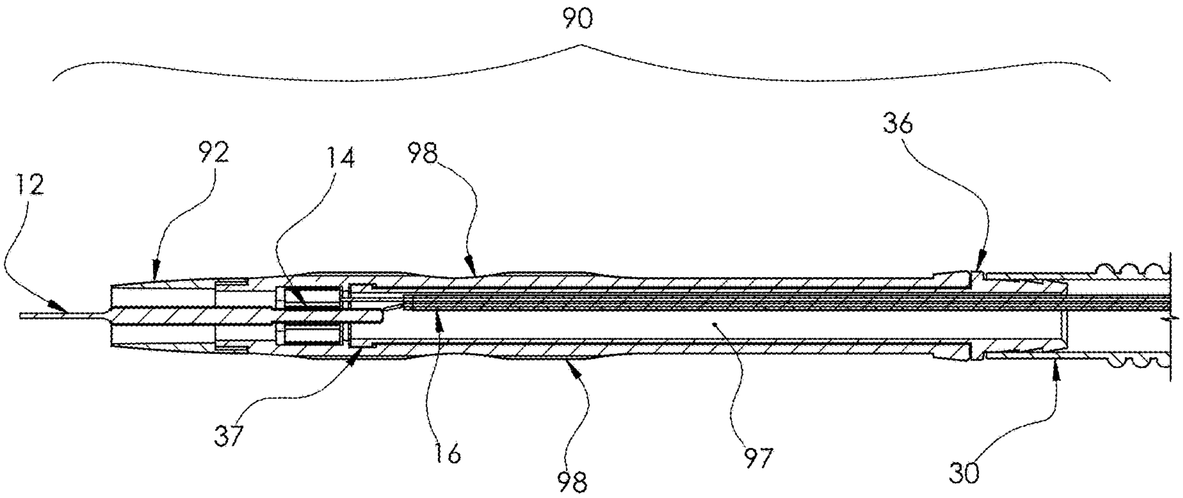
FIG. 3 is top view cross section of the invention showing a seamless rotating internal channel without seals.

FIG. 3 shows the top view cross section of the preferred embodiment of a smoke evacuating surgical pencil 90. The construction as described from distal to proximal end comprising; a metallic conductor called an active electrode 12, an active electrode socket 14 connected to a wire 16, a distal end nose 92 typically made of clear material attached to a hollow pencil body 98 of the smoke evacuating pencil 90, a one-piece near frictionless (slip fit) seamless rotating internal smoke channel 97 without friction fits or seals, having a distal inlet retaining shoulder 37 overlapping active electrode 12, and contiguously attached to the integral smoke hose fitting proximal end 36 which is longitudinally aligned with and attached to the smoke evacuating hose 30 allowing a continuous suction flow pathway. The seamless internal channel 97 can rotate because in one embodiment the active electrode socket 14 is not connected or attached to the seamless internal channel 97. In another embodiment obvious to those skilled in the art has the active electrode socket 14 in the normal location with electrical connections exiting the seamless internal channel 97 and fixedly attached behind the distal end of the seamless internal channel 97 making contact with the hand control buttons and active electrode socket 14. Seamless internal channel 97 may or may not include a telescopic section.

What is claimed:

1. A smoke evacuation pencil, comprising:

a hollow pencil body having a proximal end and a distal end;

an active electrode socket positioned in the distal end of the hollow pencil body, the active electrode socket securing an active electrode having a proximal end and a distal end, wherein the distal end of the active electrode extends beyond the distal end of the hollow pencil body; and a one-piece rotatable, seamless internal channel disposed within the hollow pencil body, the one-piece rotatable, seamless internal channel having a length that extends from a proximal end hose fitting of the one-piece rotatable, seamless internal channel to a distal inlet of the one-piece rotatable, seamless internal channel, wherein the distal inlet is positioned proximally to, and independent of, the active electrode socket while overlapping the proximal end of the active electrode;

wherein the proximal end hose fitting of the one-piece rotatable, seamless internal channel is configured to be longitudinally aligned with, and attached to, a smoke evacuation hose, and wherein the one-piece rotatable, seamless internal channel is freely rotatable within the hollow pencil body thereby establishing a continuous suction flow pathway without a need for a seal to prevent suction loss.

2. The smoke evacuation pencil of claim 1, wherein the one-piece rotatable, seamless internal channel is disposed within the hollow pencil body via a near frictionless, or slip-fit, arrangement.

3. The smoke evacuation pencil of claim 1, wherein a face of the proximal end hose fitting of the one-piece rotatable, seamless internal channel abuts a face of the proximal end of the hollow pencil body, and wherein a distal end retaining shoulder of the one-piece rotatable, seamless internal channel at the distal inlet engages a corresponding portion of the hollow pencil body to secure the one-piece rotatable, seamless internal channel within the hollow pencil body.

4. The smoke evacuation pencil of claim 1, wherein the one-piece rotatable, seamless internal channel comprises a telescopic section.

5. The smoke evacuation pencil of claim 1, wherein the active electrode socket is connected to a wire that extends through the one-piece rotatable, seamless internal channel for connection to an energy source generator.

* * * * *